United States Patent [19]

Sebastian et al.

[11] Patent Number: 4,836,194

[45] Date of Patent: * Jun. 6, 1989

[54] THERAPEUTIC LUMBOSACRAL APPLIANCE

[75] Inventors: Peter R. Sebastian, Salisbury, Md.; John L. Stump, Daphne, Ala.; Thomas V. Sebastian, Reading, Pa.

[73] Assignee: Safeguard Industrial Corporation, Leesport, Pa.

[*] Notice: The portion of the term of this patent subsequent to Nov. 3, 2004 has been disclaimed.

[21] Appl. No.: 86,316

[22] Filed: Aug. 17, 1987

Related U.S. Application Data

[63] Continuation-in-part of Ser. No. 901,559, Aug. 29, 1986, Pat. No. 4,703,750.

[51] Int. Cl.⁴ .............................................. A61F 5/02
[52] U.S. Cl. .......................................... 128/78; 2/338; 2/DIG. 6; 128/DIG. 20
[58] Field of Search .................. 128/78, 68, 69, 24 R, 128/DIG. 20; 2/338, DIG. 6

[56] References Cited

U.S. PATENT DOCUMENTS

| | | | |
|---|---|---|---|
| 1,646,590 | 10/1927 | Mildenburg | 128/78 |
| 2,104,758 | 1/1938 | Poppen | 128/DIG. 20 |
| 2,240,308 | 4/1941 | Mahe | 128/100 X |
| 2,554,337 | 5/1951 | Lampert | 128/78 X |
| 3,071,133 | 1/1963 | Eisen | 128/78 |
| 3,521,623 | 7/1970 | Nichols | 128/78 |
| 3,955,565 | 5/1976 | Johnson, Jr. | 128/DIG. 20 |
| 3,974,827 | 8/1976 | Bodeen | 128/DIG. 20 |
| 4,099,523 | 7/1978 | Lowrey | 128/75 |
| 4,120,297 | 10/1978 | Rabischong et al. | 128/78 |
| 4,135,503 | 1/1979 | Romano | 128/78 |
| 4,175,548 | 11/1979 | Henry | 128/78 X |
| 4,178,922 | 12/1979 | Curlee | 128/78 |
| 4,178,923 | 12/1979 | Curlee | 128/78 |
| 4,475,543 | 10/1984 | Brooks et al. | 128/78 |
| 4,552,135 | 11/1985 | Racz et al. | 128/78 |
| 4,559,933 | 12/1985 | Batard et al. | 128/78 |
| 4,576,154 | 3/1986 | Hyman et al. | 128/78 |
| 4,597,386 | 7/1986 | Goldstein | 128/78 |
| 4,622,957 | 11/1986 | Curlee | 128/78 |
| 4,682,587 | 7/1987 | Curlee | 128/78 |
| 4,682,588 | 7/1987 | Curlee | 128/78 |
| 4,703,750 | 11/1987 | Sebastian et al. | 128/78 |

FOREIGN PATENT DOCUMENTS

| | | |
|---|---|---|
| 2454702 | 5/1976 | Fed. Rep. of Germany . |
| 90062 | 5/1870 | France . |
| 1461408 | 12/1966 | France . |
| 985591 | 3/1965 | United Kingdom . |

Primary Examiner—Edgar S. Burr
Assistant Examiner—Moshe I. Cohen
Attorney, Agent, or Firm—Wenderoth, Lind & Ponack

[57] ABSTRACT

A therapeutic appliance for application to the lumbar spine and which follows the contours of the iliac crests and overlies the sacrum and sacroiliac joints as well as anchors below the posterior superior iliac spines of the human body including an external shell having a length sufficient to extend around the abdominal region of the body with fasteners at opposite ends of the shell and an air bladder disposed on the shell. The air bladder has a plurality of air chambers including elongated air chambers which extend transversely to the longitudinal direction of the shell with lower ends thereof shaped to lie above the iliac crests, a lower longitudinally extending air chamber and an anchoring air chamber between the longitudinally extending air chamber and the outer edge of the bladder, the anchoring air chamber extending arcuately from a central portion of the air bladder towards the opposite ends of the shell and positioned to lie below the posterior superior iliac spines to prevent upward riding of the therapeutic appliance when in place on the human body and to provide support for the sacroiliac joints. The appliance may also include belts on the outside thereof for tightening the air chambers against the wearer's lumbar spine and sacroiliac joints and pockets can be provided on the inside of the appliance for applying hot or cold packs to the back muscles of the wearer of the appliance.

24 Claims, 6 Drawing Sheets

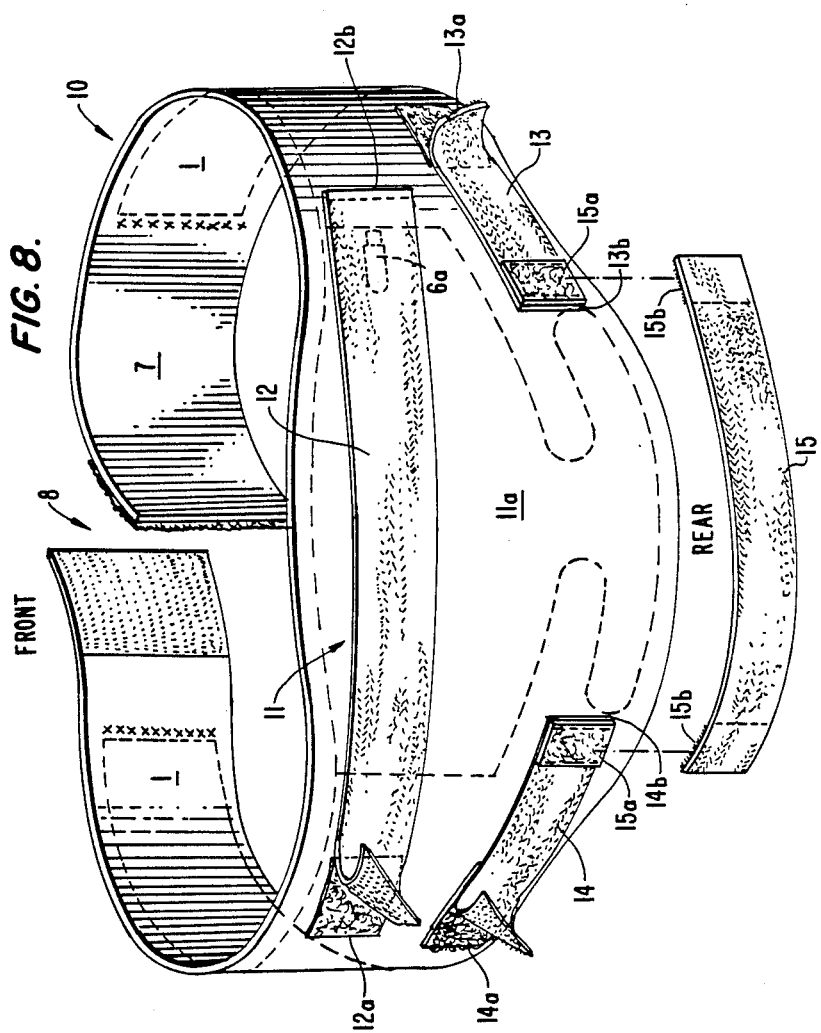

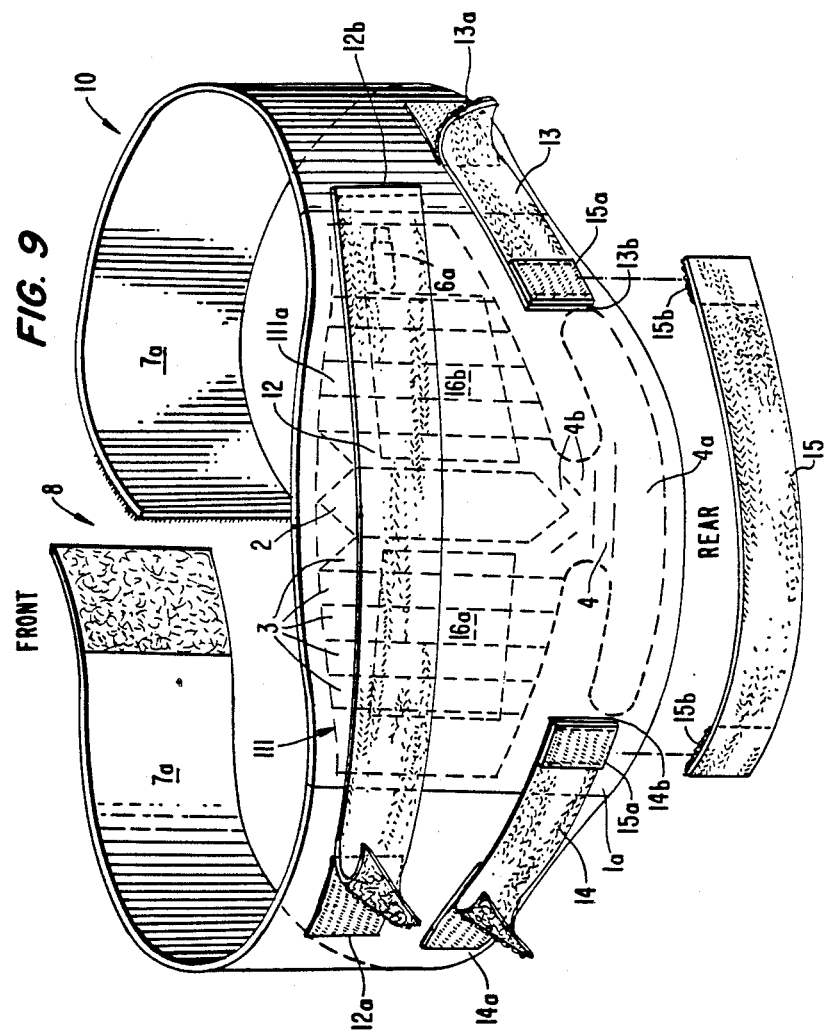

THERAPEUTIC LUMBOSACRAL APPLIANCE

This is a continuation-in-part application of Ser. No. 901,559, filed on Aug. 29, 1986 now U.S. Pat. No. 4,703,750.

FIELD OF THE INVENTION

The present invention relates to a lumbosacral therapeutic appliance designed to relieve pain in the areas of the lumbosacral spine and sacroiliac joints by maintaining normal alignment of the osseous structures and providing static stretch to paravertebral muscles to alleviate unwanted muscle spasms and fatigue.

BACKGROUND OF THE INVENTION

The problem of low back pain is commonly a result of mechanical and physiologic derangements of the osseous ligamentous and muscular structures of this region. The low back for purposes of this discussion refers to the area of the lumbar and sacral portions of the spinal column and the sacroiliac joints. The interrelationships between the osseous, ligamentous and muscular structures is highly important in this area of the spine which is responsible for considerable weight bearing and structural support.

Injury to one or more of these three elements commonly results in dysfunction and subsequent pain in the others. Also, injury at one level of the spine may affect adjacent segments leading to dysfunction distant to the original abnormality or site of injury. Proper posture for optimal function is the result of correct vertebral alignment, balanced ligamentous support and limitation of excessive or unwanted movement, and flexibly balanced, strong musculature regulating and stabilizing motion.

While these objectives may be met by a variety of therapeutic modalities, low back braces used for this purpose should have certain characteristics, such as (1) contour fitting of the normal spinal/pelvic curvatures; (2) sufficient firmness to prevent buckling or unwanted binding of the appliance during wearer movement; (3) adequate flexibility to allow free and unrestricted normal range of motion; (4) adequate coverage of anatomically and functionally related segments of the spine where therapeutic forces are needed for maximal effectiveness; and (5) contour shaping of the pelvic segment to avoid unwanted bony bridging effect of the iliac crests which inhibits desired counter-pressure over midline and adjacent paravertebral muscles and osseous elements. The prior art therapeutic air inflated appliances fail in one or more of these areas of therapeutic principles.

BRIEF SUMMARY OF THE INVENTION

The present invention provides a new and improved lumbosacral therapeutic appliance designed to relieve pain in the areas of the lumbosacral spine and sacroiliac joints by maintaining normal alignment of the osseous structures and providing static stretch to paravertebral muscles to alleviate unwanted muscle spasms and fatigue. The device of the present invention can perform this function without limitation of the normal motion of the wearer. In addition, this device provides full coverage over the above mentioned structures by being form fitted to the contours of the area while avoiding unwanted bony bridging.

The device of the present invention includes an air bladder contoured to fit among the bony structures by means of central air chambers which overlie the midline of the lumbar spine extending down to the sacrum. The device also includes transversely extending chambers which follow the contour of the iliac crests and longitudinally extended air chambers which overlie the sacrum and lie between the sacroiliac joints as well as air chambers which lie just beneath the posterior superior iliac spines and serve to also anchor and prevent upward riding of the appliance and provide support for the sacroiliac joints.

The device of the present invention also contains a more readily accessible means of altering air chamber pressure through an air conduit/valve mechanism even when the appliance is worn under clothing.

BRIEF DESCRIPTION OF THE DRAWINGS

Details of the invention are shown by the following description of several embodiments with reference to the figures in the drawings, in which are shown:

FIG. 6 is a more detailed view of FIG. 5a.

FIG. 8 shows a second embodiment of the present invention which includes air bladder tightening means.

FIG. 9 shows a third embodiment of the present invention which includes pockets inside the shell of the therapeutic appliance for holding hot packs or cold packs to apply heating or cooling, respectively, to the sacro lumbar region of a wearer of the device according to the present invention.

DETAILED DESCRIPTION OF THE PREFERRED EMBODIMENTS

Figure 1:
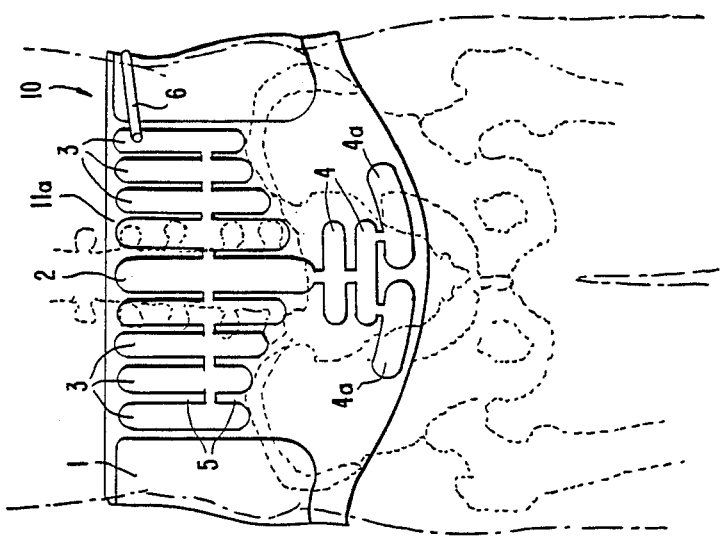
FIG. 1 illustrates the lower part of the throacic spine, the lumbar spine, the sacrum, the sacroiliac joints, the iliac crests and the posterior superior iliac spine.
Figure 2:
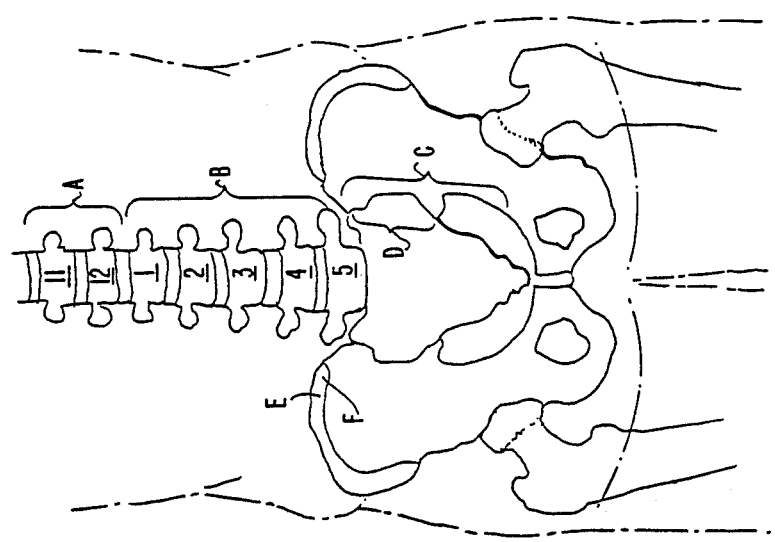
FIG. 2 illustrates a cut-away view of the device according to the present invention showing the relationship of the air bladder to the lumbosacral spine and sacroiliac joints.

The therapeutic appliance of the present invention is generally indicated at 10 in FIGS. 2 and 4. FIG. 1 illustrates the areas anatomically underlying the therapeutic appliance. These areas are those intended to be therapeutically affected by the appliance. The lumbar spine (B) consists of five vertebrae in normal subjects, each separated by an intervening intervertebral disc. The sacrum (C) consists of five anatomically fused segments. The sacroiliac joints (D) represents the articulation of the sacrum and iliac bones on each side. The iliac crest (E) is that portion of the iliac bone lying highest and ending in the posterior superior iliac spine (F) which is the most posterior bony protuberence. Both (E) and (F) may hold prior art appliances away from the spine and paravertebral musculature to be treated thus diminishing the intended therapeutic counter-pressure.

Figure 3:
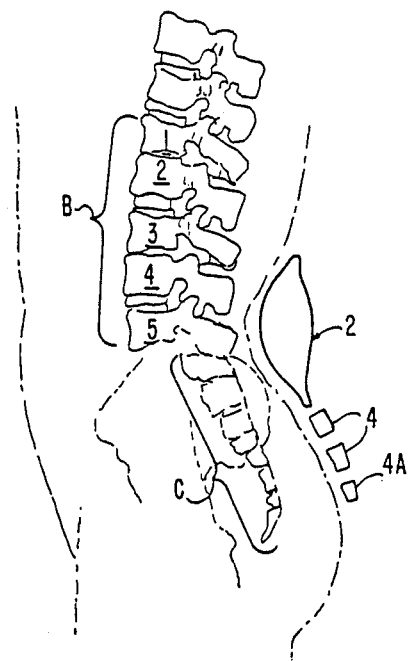
FIG. 3 shows a side view of the spine and the positions of the air chambers of the device according to the present invention.

The therapeutic appliance 10 of the present invention comprises a belt which extends in a longitudinal direction and an air bladder 11 which includes a number of air chambers shown generally at 11a and a non-air filled segment 1 of the bladder, as shown in FIG. 2. The air chambers preferably are $\frac{3}{4}$ to $1\frac{1}{2}$ inches in width in the longitudinal direction when uninflated and comprise a central transversely extending air chamber 2 which overlies the midline of the lumbar spine and which extends vertically down to the sacrum. On either side of the central air chamber 2 are more laterally placed air chambers 3 which have lower ends which extend in an arcuate path and follow the contour of the iliac crests. The upper ends of the air chambers 2 and 3 can be substantially parallel to each other as shown in FIG. 2 or can lie along a path which tapers from the central air chamber 2 towards opposite ends of a modified air bladder 111, such that the lengths of the air chambers 3 become longer towards the central air chamber 2, as shown in FIG. 9. Below the central air chamber 2 are at least one longitudinally extending air chamber 4 which overlies the sacrum and lies between the sacroiliac joints and arcuately extending anchoring air chambers 4a which overlie the sacroiliac joints and which lie just beneath the posterior superior iliac spines and serve additionally as anchors to prevent upward riding of the appliance and also provide support for the sacroiliac joints. The air chambers are separated by a heat sealed or sewn portion of the bladder material. It can be seen from FIGS. 4a and 4b that the non-air filled segment 1 of the air bladder 11 extends around a shell 7 of the therapeutic device terminating short of a closure device 8. The contoured fit of the air chambers when inflated are shaped to maintain the normal lordotic curvature of the individual wearer's spine as can be seen in FIG. 3. The modified air bladder 111 shown in FIG. 9 includes a central air chamber 2 having a width greater than the air chambers 3 and diagonally extending chambers 4b connect the air chambers 3 on either side of the central chamber 2 to the longitudinally extending chamber 4. The diagonally extending chambers are smaller in width than air chambers 3 and 4 to allow flexibility of the appliance in the area directly below and to either side of the central air chamber 2.

Figure 4A:
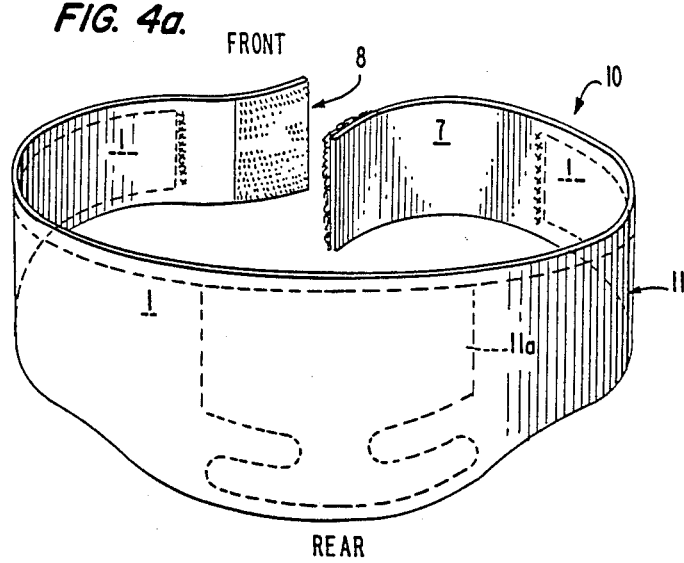
FIG. 4a shows a perspective view of the device according to the present invention with an external shell enclosing the air bladder.
Figure 4B:
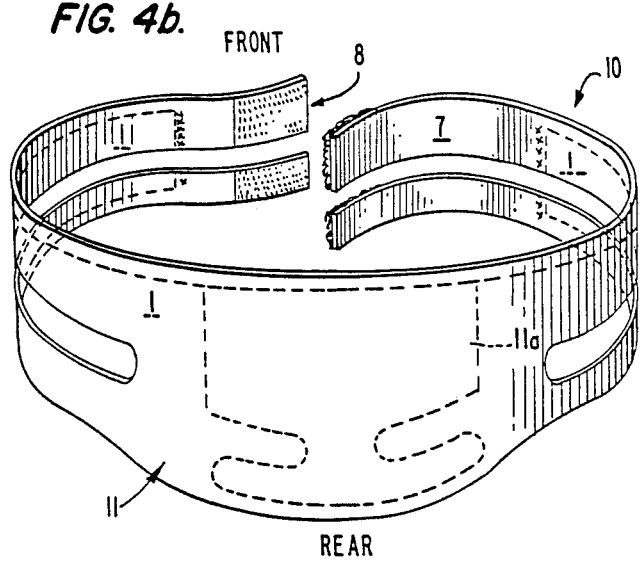
FIG. 4b shows a perspective view of another embodiment of the device according to the present invention with the external shell being separated into two elongated sections on either side of the air bladder.
Figure 5B:
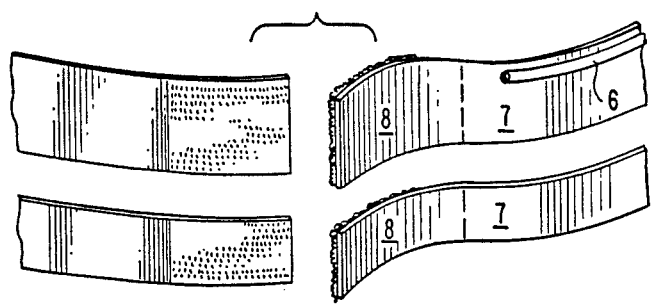
FIG. 5b is a perspective view of the device shown in FIG. 4b which shows the outlet for an air conduit located near an upper front closure.
Figure 5A:
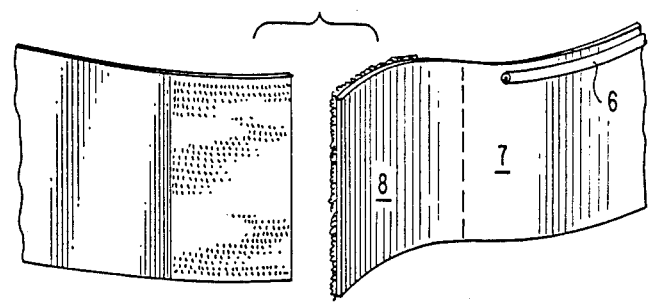
FIG. 5a is a perspective view of the device according to the present invention which shows the outlet for an air conduit located near the front closure.

The external shell 7 of the therapeutic device of the present invention is composed of a washable moisture absorbent fabric which allows the device to be worn inside or outside of the wearer's clothing. The external shell 7 assumes the same basic shape of the contained air bladder 11 which it protects. The bladder 11 is fabricated from a nylon or plastic/vinyl material with low stretchability to allow repeated reproduction of the same air chamber configuration each time the air chambers are inflated. The therapeutic appliance can be secured over the wearer's trunk by a single closure device 8 which can be a VELCRO type of attachment, as shown in FIGS. 4a and 5a, or the external shell can be separated into an upper and lower section which extend longitudinally from adjacent the bladder 11 with a space therebetween and with a closure device at the free end of each section, as shown in FIGS. 4b and 5b. Alternatively, other fastening means such as buckles, snaps or lace-up type of attachment means can be used.

FIG. 3 shows a midline sagital section of the inflated central air chambers having a tapered upper and lower end with a broad central section of the vertically aligned lumbar chamber intended to aid in the maintenance of the normal lumbar lordotic curvature. Alternatively, other configurations of the inflated air chambers are within the scope of the present invention.

Figure 6:
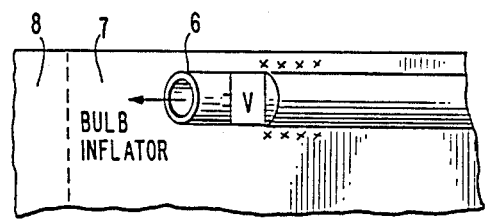

FIG. 5a shows the position of an air conduit 6 in the upper margin of the external shell 7 where it exits to the external surface of the shell or the air conduit can be located in the upper section of the external shell, as shown in FIG. 5b. However, the air conduit 6 can be located anywhere within the bladder 11. An enlarged drawing of the outlet of the air conduit 6 is shown in FIG. 6 wherein a valve (V) is shown within the air conduit for maintaining inflation at a desired level. Also, not shown is an air pump, such as a bulb inflater, which can be attached to the outlet of the air conduit 6 for inflation of the air chambers.

Figure 7:
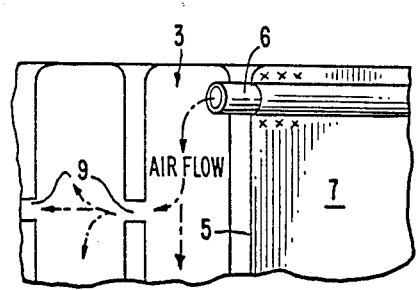
FIG. 7 is a cut-away view showing the connection of the air conduit to the air chambers.

FIG. 7 shows the entry of the air conduit 6 into a laterally placed chamber 3. The air conduit 6 is held in position within the bladder 11 and in fluid communication with at least one of the air chambers 11a by heat sealing or sewing a segment 5 of the air bladder 11. Air passes freely form the air conduit 6 into one of the air chambers, such as a lateral chamber 3, and then through openings 9 between the air chambers for allowing the air to fill all chambers within the bladder.

FIG. 8 shows a modification of the therapeutic lumbosacral appliance wherein the external shell 7 comprises end sections 7a and an intermediate section 7b, the section 7b being of a washable moisture absorbent fabric which allows the device to be worn inside or outside of the wearer's clothing and section 7b has the same dimensions as that of the modified air bladder 111 shown in FIG. 9. The modified air bladder 111 is slightly larger in length than the length in the longitudinal direction of the air chambers 11a shown in FIG. 4a of the present invention. The air bladder 111 can include the configuration of air chambers as are shown in FIG. 2 of the present invention or these chambers can be modified to have other configurations such as that shown in FIG. 9. The section 7b of the shell 7 is attached at both longitudinal ends thereof to respective ends of the sections 7a, each of which is formed from a four-way stretch material such as neoprene or latex optionally coated on one or both sides with a nylon fabric such as a looped plush polyester. Alternatively, the sections 7a can be of a semi-rigid sheet of material such as a woven nylon webbing. The closure device 8, such as a VELCRO type of attachment, is provided at the free ends of the sections 7a.

The second preferred embodiment shown in FIGS. 8 and 9 also includes air bladder tightening means comprising the uninflated portion 1, 1a of the air bladder 11, 111 and any one or more of belts 12, 13, 14 and 15. The first belt 12 is attached at one end thereof to the shell 7 at a position to overlie the air chambers 2 and 3. For instance, one end 2b of the belt 12 can be attached adjacent one longitudinal end of the air chambers 11a, 111a and the other end 12a of the belt 12 can be adjustably attached by suitable means located on the section 7a of the shell 7 located adjacent the other longitudinal end of the air chambers 11a, 111a. Suitable adjustable connection means can comprise a VELCRO type attachment with the respective hook and loop sections being located on the free end 12a of the strap 12 and the section 7a of the shell 7. The function of the belt 12 is to press the upper air chambers 2, 3 tightly against the lumbar spine with the lower ends of the air chambers 3 extending in an arcuate path above the iliac crests. The belt 12 provides additional support since the length of the air chambers 2 and 3 bend the upper ends thereof tend to bend due to the curvature of the wearer's back, and without the belt 12 the upper ends of air chambers 2 and 3 are bent outwardly away from the body of the wearer when they are inflated. The belt 12 cooperates with the uninflated portion of the air bladder 1, 1a to thereby tighten the air chambers against the lumbar spine.

A pair of belts 13, 14 are provided on either side of the anchoring air chamber 4a to hold the anchoring air chamber 4a tightly against the sacroiliac joints just beneath the posterior superior iliac spines to thereby assist the anchoring air chamber 4a in preventing upward riding of the appliance and also to provide additional support for the sacroiliac joints. The belts 13, 14 can be attached at one end 13b, 14b thereof to a portion of the air bladder 1a adjacent to opposite longitudinal ends of the anchoring air chamber 4a. The free ends 13a, 14a of each of the straps 13, 14 can be attached by suitable means, such as VELCRO type hook and loop sections, to a portion of one of the sections 7a of the shell. A suitable length for the straps 13, 14 can be about 8 inches or any other suitable dimension. Likewise, a suitable length for the strap 12 can be 20 inches or any suitable dimension depending upon the particular shape of the wearer of the therapeutic lumbosacral appliance.

An optional belt 15 can be provided to overlie the anchoring air chamber 4a. Suitable means for attaching the optional belt 15 can comprise a VELCRO type attachment with the respective hook and loop sections 15a, 15b being applied to the fixed ends of the belts 13, 14 and the free ends of the optional strap 15.

In the modification shown in FIG. 8, the air conduit 6 terminates in a suitable air valve 6a which is provided to extend outwardly from the air bladder 1a and through a suitably sized hole in the upper belt 12. Of course, the air valve 6a can be provided at any suitable location on the air bladder 1a or the air conduit 6 can extend around the shell 7 to another suitable location with the air valve 6a located at the end thereof.

Another modification of the present invention is shown in FIG. 9 wherein inside pockets are disposed on the first section 7b of the shell 7. These pockets 16a, 16b are provided for holding suitable cooling pad for applying cooling to the sacrolumbar region or the pockets can be used for holding hot packs to apply heat to the sacrolumbar region.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A therapeutic appliance for application to the lumbar spine and which follows the contours of the iliac crests and overlies the sacrum and sacroiliac joints as well as anchors below the posterior superior iliac spines of the human body, the appliance comprising:
   an external shell having a length in a longitudinal direction sufficient to extend around and encircle the abdominal region of the body, said shell having closure means at opposite ends thereof for attaching said ends together;
   an air bladder disposed on said external shell, said air bladder having a plurality of air chambers located centrally between said opposite ends of said shell, said air chambers including elongated air chambers which extend transversely to said longitudinal direction, the lower ends of which extend in an arcuate path on each side of a central portion of said air bladder and which are shaped to lie above the iliac crests, and at least one anchoring air chamber extending arcuately between said transversely extending air chambers and an outer edge of said bladder, said anchoring air chamber extending from said central portion of said air bladder toward said opposite ends of said shell and positioned to lie below the posterior superior iliac spines to prevent upward riding of said therapeutic appliance when inflated and in place on the human body and provide support to the sacroiliac joints;
   means for tightening said air chambers against the body of a wearer of the appliance; and
   air conduit means for inflating said air chambers with air.

2. The therapeutic appliance of claim 1, wherein the at least one anchoring air chamber comprises a pair of arcuately extending air chambers each of which extends towards a respective one of said opposite ends of said external shell.

3. The therapeutic appliance of claim 1, wherein said tightening means is disposed on said external shell for tightening said elongated air chambers against the lumbar spine of a wearer of the appliance.

4. The therapeutic appliance of claim 1, wherein said air bladder is a plastic material having low stretchability to allow accurate reproduction of the configuration of said air chambers, each of said air chambers being separated by a joint between an inner and outer layer of said air bladder.

5. The therapeutic appliance of claim 1, wherein said tightening means is disposed on said external shell for tightening said at least one anchoring air chamber against the sacroiliac joints of a wearer of the appliance.

6. The therapeutic appliance of claim 1, further comprising means disposed on said external shell for holding a hot pack or cold pack against the back muscles of a wearer of the device.

7. The therapeutic appliance of claim 1, wherein said shell is a washable moisture absorbent fabric material.

8. The therapeutic appliance of claim 1, wherein said air conduit means includes an air conduit having a valve at an outlet end thereof, said outlet end being adapted for connection to an air pump for filling said air chambers with air.

9. The therapeutic appliance of claim 1, wherein said external shell is divided on each side of said air bladder into an upper and a lower longitudinally extending section with a space therebetween, said upper section and said lower section each having a closure means at a free end thereof.

10. The therapeutic appliance of claim 1, wherein said air bladder further comprises at least one elongated air chamber which extends in said longitudinal direction and which is disposed between said lower ends of said transversely extending air chambers and said at least one anchoring air chamber.

11. The therapeutic appliance of claim 10, wherein the at least one anchoring air chamber comprises a pair or arcuately extending air chambers each of which extends towards a respective one of said opposite ends of said external shell.

12. The therapeutic appliance of claim 10, wherein said at least one longitudinally extending air chamber comprises a pair of air chambers which are spaced apart from each other in a direction transverse to said longitudinal direction.

13. The therapeutic appliance of claim 10, wherein said air bladder is a plastic material having low stretchability to allow accurate reproduction of the configurations of said air chambers, each of said air chambers being separated by a joint between an inner and outer layer of said air bladder.

14. The therapeutic appliance of claim 10, wherein said tightening means is disposed on said external shell for tightening said elongated air chambers against the lumbar spine of a wearer of the appliance.

15. The therapeutic appliance of claim 10, wherein said tightening means is disposed on said external shell for tightening said at least one anchoring air chamber against the sacroiliac joints of a wearer of the appliance.

16. The therapeutic appliance of claim 10, wherein said shell is a washable moisture absorbent fabric material.

17. The therapeutic appliance of claim 10, wherein said air conduit means includes an air conduit having a valve at an outlet end thereof, said outlet end being adapted for connection to an air pump for filling said air chambers with air.

18. The therapeutic appliance of claim 10, further comprising means disposed on said external shell for holding a hot pack or cold pack against the back muscles of a wearer of the device.

19. The therapeutic appliance of claim 10, wherein said external shell is divided on each side of said air bladder into an upper and a lower longitudinally extending section with a space therebetween, said upper section and said lower section each having a closure means at a free end thereof.

20. A therapeutic appliance for application to the lumbar spine and which follows the contours of the iliac crests and overlies the sacrum and sacroiliac joints of the human body, the appliance comprising:
an external shell having a length in a longitudinal direction sufficient to extend around and encircle the abdominal region of the body, said shell having closure means at opposite ends thereof for attaching said ends together;
an air bladder disposed on said external shell, said air bladder having a plurality of air chambers located centrally between said opposite ends of said shell, said air chambers including elongated air chambers which extend transversely to said longitudinal direction, said air chambers each having a lower end, the lower ends terminating in an arcuate path which rises on each side of a central portion as it increases in distance from said center portion of said air bladder, said arcuate path being shaped to lie above and adjacent the iliac crests;
means for tightening said air chambers against the lumbar spine of a wearer of the appliance; and
air conduit means for inflating said air chambers with air.

21. The therapeutic appliance of claim 20, wherein said external shell comprises a first section on which said air bladder is disposed and two second sections, each of which is attached at one end thereof to said first section, said closure means being disposed on the free ends of said second sections.

22. The therapeutic appliance of claim 20, wherein said tightening means comprises at least one belt extending across said air chambers and adjustably attached to said external shell for varying the degree of tightening thereof.

23. A therapeutic appliance for application to the lumbar spine and which follows the contours of the iliac crests and overlies the sacrum and sacroiliac joints as well as anchors below the posterior superior iliac spines of the human body, the appliance comprising:
an external shell having a length in a longitudinal direction sufficient to extend around and encircle the abdominal region of the body, said shell having closure means at opposite ends thereof for attaching said ends together;
an air bladder disposed on said external shell, said air bladder having a plurality of air chambers located centrally between said opposite ends of said shell, said air chambers including elongated air chambers which extend transversely to said longitudinal direction, said air chambers each having a lower end, and anchoring air chamber means for preventing upward riding of said therapeutic appliance when said air bladder is inflated and in place on a human body and providing support to the sacroiliac joints, said anchoring air chamber means comprising at least one anchoring air chamber extending arcuately between said lower ends of said transversely extending air chambers and a longitudinally extending outer edge of said air bladder, said anchoring air chamber means extending from said central portion of said air bladder toward said opposite ends of said shell and positioned to lie below the posterior superior iliac spines; and
air conduit means for inflating said air chambers with air.

24. The therapeutic appliance of claim 23, wherein the at least one anchoring air chamber comprises a pair of arcuately extending air chambers each of which extends towards a respective one of said opposite ends of said external shell.

* * * * *